252-95 AU 166 EX
1/13/81 XR 4,245,125

United States Patent [19]

Wirth et al.

[11] 4,245,125

[45] Jan. 13, 1981

[54] NOVEL ADDUCTS

[75] Inventors: Hermann O. Wirth, Bensheim; Hans-Helmut Friedrich, Lautertal, both of Fed. Rep. of Germany

[73] Assignee: Ciba-Geigy Corporation, Ardsley, N.Y.

[21] Appl. No.: 37,599

[22] Filed: May 10, 1979

[30] Foreign Application Priority Data

May 18, 1978 [CH] Switzerland ........................ 5391/78
Aug. 4, 1978 [CH] Switzerland ........................ 8360/78

[51] Int. Cl.[3] ...................... C07C 43/10; C07C 43/11; C08F 120/18; C08F 2/00

[52] U.S. Cl. .................................. 568/680; 568/558; 568/579; 568/623; 568/648; 568/679; 568/852; 260/348.16; 71/69; 252/95; 252/186; 521/209; 521/329.7; 568/21; 568/32; 568/608

[58] Field of Search .................. 252/95, 186; 568/579, 568/680, 679, 559, 558, 623; 423/272, 584

[56] References Cited

U.S. PATENT DOCUMENTS

| | | | |
|---|---|---|---|
| 3,194,768 | 7/1965 | Lindner et al. | 423/272 |
| 3,345,303 | 10/1967 | Schmid et al. | 252/95 |
| 3,933,982 | 1/1976 | Kushibe | 423/272 |
| 3,970,575 | 7/1976 | Barrett | 252/95 |

*Primary Examiner*—Howard T. Mars
*Attorney, Agent, or Firm*—Luther A. R. Hall

[57] ABSTRACT

Compounds of the formula I $$A \cdot m\ B \quad (I)$$

wherein

A is a compound of the formula II or III $$R_1-Y-\underset{OH}{\underset{|}{CH}}-\underset{OH}{\underset{|}{CHR_2}}, \quad (II) \qquad R_1-X-(CH_2-Q-O)_n-H \quad (III)$$

m is a rational number between 0.1 and 4.0, and

B is $H_2O_2$, $N_2H_4$ or $NH_2OH$, and $R_1$ is an unsubstituted or substituted aliphatic or aromatic hydrocarbon radical which has 3-30 C atoms and which can be interrupted by oxygen or sulfur atoms, $R_2$ is hydrogen or $C_1$-$C_{30}$ alkyl, X is —O— or —$SO_2$— and, in the case where B is $N_2H_4$ or $NH_2OH$, also —S— or —SO—, Y is the direct bond, $$-CH(OH)- \text{ or } -\overset{O}{\overset{\|}{C}}-O-CH_2-,$$

Q is —$CH_2$, —CH(OH)—$CH_2$— or —CH($CH_2$—OH)—, and n is 1, 2, 3, 4, 5, 6, 7 or 8.

4 Claims, No Drawings

NOVEL ADDUCTS

The present invention relates to novel adducts of hydrogen peroxide, hydrazine and hydroxylamine with glycerol monoethers, and with related compounds having a 1,2-diol structure, and also with ethylene oxide adducts, to their production as well as to their general applicability as redox partners in electron transfer reactions, particularly also in the case of polymerization reactions.

The high activity of hydrogen peroxide, hydazine and hydroxylamine in redox processes has been known for a long time. These hydrophilic inorganic compounds have of course disadvantages which greatly limit their usefulness. Thus, for example, these substances are scarcely soluble in organic solvents, especially in the less polar solvents. Furthermore, it is known that hydrogen peroxide, hydrazine and hydroxylamine readily decompose, frequently even in an explosive manner. Many attempts have therefore already been made to avoid the stated disadvantages by providing chemical derivatives. There have thus appeared on the market organic peroxides (for example commercial dicumyl peroxide) which are soluble in nonpolar organic solvents, and which moreover have really good thermal stability, but which leave much to be desired with respect to their activity as redox partners. On the other hand, there are offered commercially relatively expensive hydroperoxides which are more active than the organic peroxides, but which have a decomposition tendency that again is considerably greater, so that storage and transport create problems similar to those met with in the case of the free inorganic compounds. Further attempts have been made with addition compounds (for example with urea/hydrogen peroxide). Adducts of this type have however only extremely limited solubility in organic solvents.

There has now been found a class of adducts of hydrogen peroxide, hydrazine and hydroxylamine with glycerol monoethers and with related compounds having a 1,2-diol structure, which adducts combine high solubility even in highly nonpolar organic solvents, intense activity as redox partners and a stability surprisingly high for chemical addition compounds.

The novel adducts correspond to the formula I $$A \cdot mB \qquad (I)$$

wherein

A is a compound of the formula II or III

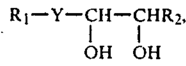

(II)

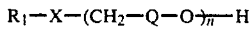

(III)

m is a rotional number between 0.1 and 4.0, and

B is $H_2O_2$, $N_2H_4$ or $NH_2OH$, and $R_1$ is an unsubstituted or substituted aliphatic or aromatic hydrocarbon radical which has 3—30 C. atoms and which can be interrupted by oxygen or sulfur atoms, $R_2$ is hydrogen or $C_1$-$C_{30}$ alkyl, X is —O— or —$SO_2$— and, in the case where B is $N_2H_4$ or $NH_2OH$, also —S— or —SO—, Y is the direct bond,

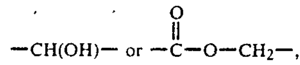

Q is —$CH_2$—, —CH(OH)—$CH_2$— or —CH($CH_2$—OH)— and n is 1, 2, 3, 4, 5, 6, 7 or 8.

A is a compound of the formula II or III, which formulae possess, as a common characteristic, a vicinal diol group or an ethylene oxide group, which is in particular a terminal group.

In the formulae II and III, $R_1$ is a hydrocarbon radical of aliphatic or aromatic character, which has 3-30, preferably 3-20 and especially 5-18, C atoms, which can be interrupted by oxygen or sulfur atoms, and which can be unsubstituted or substituted. If $R_1$ is an unsubstituted or substituted aliphatic or aromatic hydrocarbon radical, it is straight-chain or in particular branched-chain, preferably branched-long-chain alkyl, or cycloalkyl, cycloalkylalkyl, aryl or aralkyl, in each case substituted by 1-3 alkyl groups having a total of 1-12 C atoms. Examples of $R_1$ are n-propyl, isopropyl, n-butyl, sec-butyl, tert-butyl, n-pentyl, tert-pentyl, n-hexyl, isohexyl, 2-ethylbutyl, n-octyl, 1,1,3,3-tetramethylbutyl or 2-ethylhexyl; or straight-chain or branched-chain isomers of nonyl, decyl, undecyl, dodecyl, tetradecyl, hexadecyl, octadecyl, eicosyl, docosyl, tetracosyl or triacontyl, and in this respect mixtures of isomers can just as well be used. Particularly suitable are branched-chain alkyl groups which are derived from commercial alcohols, for example from Guebert alcohols and Alfoles (manufacturer: Condea), Dobanoles (manufactuerer: Shell) or Oxanoles (manufacturer: Ruhr-Chemie). If $R_2$ is $C_1$-$C_{30}$ alkyl, it is for example methyl or ethyl, or $R_2$ can have a meaning given for $R_1$ as alkyl. As cycloalkyl, $R_1$ preferably contains 5-8 C atoms, such as in cyclopentyl, cycloheptyl, cyclooctyl or, in particular, in cyclohexyl. $R_1$ as aryl is preferably phenyl, and as aralkyl it is preferably benzyl. If $R_1$ as cycloalkyl, cycloalkylalkyl, aryl or aralkyl having 1 to 3 alkyl groups with a total of 1-12 C atoms is substituted, the substituents are for example: methyl, ethyl, iso-propyl, tert-butyl, sec-butyl, tert-pentyl, 1,1,3,3-tetramethylbutyl, nonyl or 1,1,3,3,5,5,-hexamethylhexyl. Examples of $R_1$ as alkyl-substituted cycloalkyl, cycloalkylalkyl, aryl or aralkyl are cyclohexylethyl, cycloheptylmethyl, cyclohexylmethyl, 2,4-dimethylcyclohexyl, 2,6-ditert-butylphenyl, 4-nonylphenyl, 2,4,6,-tritert-butylphenyl, 2-tert-butyl-4-methylphenyl or 4-ethylbenzyl.

Aliphatic or aromatic hydrocarbon radicals $R_1$ which are interrupted by oxygen or sulfur atoms are preferably alkyl groups interrupted by oxygen or sulfur atoms, and in particular those which are derived from reaction products from alcohols or mercaptans with ethylene oxide and/or propylene oxide. There are formed in this manner especially radicals of the cellosolve or carbitol type, such as the methyl-cellosolve derivative $CH_3$—O—$CH_2$—$CH_2$— or the methyl-carbitol derivative $CH_3$—O—$CH_2$—$CH_2$—O—$CH_2$—$CH_2$—. Within the C numbers are given above, there are meant polyether or polythioether groups having up to 15 hetero atoms.

In preferred compounds, the radicals $R_1$ and $R_2$ together have no more than 30 C atoms.

X is —O— or —$SO_2$— and, in the case where hydrazine adducts or hydroxylamine adducts are concerned, also —S— or —SO—. Under the conditions stated, the preferred meaning of X is —S— or in particular —O—.

Y can be the direct bond,

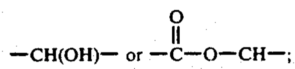

$-CH(OH)-$ or $-\overset{O}{\overset{\|}{C}}-O-CH-$;

Y is preferably —CH(OH) and especially the direct bond.

The index n can be an integer 1,2,3,4,5,6,7 or 8, but is preferably 1 or 2, particularly however it is 1. It is a preferred subject matter of the invention that mixtures of compounds having different n values are used. The value n signifies therefore for the mixtures a statistical mean value which can be expressed by a rational number of $>1$ to 6, preferably from 1 to 4, but especially 1 to 2. This statistical value is denoted in the following by $\bar{n}$.

With the index m is defined the addition ratio of B to A. This ratio B:A varies between 10:1 and 1:3, and is preferably 1.25:1 to 1:2. The value of m can therefore be expressed by a rational number 0.1 to 4.0, preferably 0.8 to 2.0.

The symbol B indicates which redox component is involved. The preferred meaning of B is $H_2O_2$.

It is possible that the compounds of the formula I contain an amount of water. The number of water particles present in the molecule should not as a rule exceed the value m. Anhydrous substances are largely preferred.

Of particular interest are compounds of the formula I wherein

- m is a rational number between 0.8 and 4.0,
- $R_1$ is $C_3$-$C_{20}$ alkyl which can be interrupted by oxygen of sulfur atoms, or it is cyclohexyl, cyclohexylmethyl or cyclohexylethyl, in each case unsubstituted or substituted by 1 to 3 alkyl groups having a total of 1-12 C atoms,
- $R_2$—is hydrogen,
- X —is —O— or, in the case where B is $N_2H_4$ or $NH_2OH$, also —S—,
- Y—is the direct bond or —CH(OH)—,
- n—is 1 or 2, and
- A, B and Q have the meanings defined above.

Preferred compounds of the formula I are those wherein

- A—is a group of the formula III,
- m—is a rational number between 0.8 and 4.0,
- $R_1$—is $C_3$-$C_{15}$ alkyl,
- X—is —O—,
- N—is 1 or 2, and
- B and Q have the meanings defined above.

Examples of compounds of the formula I are:

(1) $Z-O-CH_2-CH(OH)-CH_2(OH)\ .\ 2B$
(2) $i\text{-}C_{13}H_{27}-O-CH_2-CH(OH)-CH_2(OH)\ .\ 2B$
(3) $n\text{-}C_{18}H_{37}-O\text{+}CH_2-Q-O\text{+}_7H\ .\ 2B$
(4) $n\text{-}C_{13\text{-}16}H_{27\text{-}33}-CH(OH)-CH_2(OH)\ .\ 2B$
(5) $Z-O\text{+}CH_2-Q-O\text{+}_2H\ .\ B$
(6) $Z-O-CH_2-CH(OH)-CH_2(OH)\ .\ B$
(7) $i\text{-}C_5H_{11}-O-CH_2-CH(OH)-CH_2(OH)\ .\ 2B$
(8) $n\text{-}C_{12}H_{25}-O-CH_2-CH(OH)-CH_2(OH)\ .\ 2B$

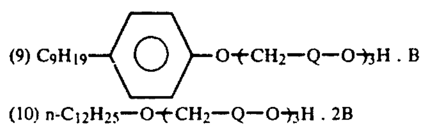

(9) $C_9H_{19}-C_6H_4-O\text{+}CH_2-Q-O\text{+}_3H\ .\ B$

(10) $n\text{-}C_{12}H_{25}-O\text{+}CH_2-Q-O\text{+}_3H\ .\ 2B$

-continued

(11) $\text{[branched alkyl]}-S-CH_2-CH(OH)-CH_2(OH)\ .\ B$
(12) $n\text{-}C_5H_{11}-O-CH_2-CH(OH)-CH_2(OH)\ .\ B$
(13) $n\text{-}C_{12}H_{25}-S-CH_2-CH(OH)-CH_2(OH)\ .\ 2B$
(14) $n\text{-}C_{18}H_{37}-O\text{+}CH_2-Q-O\text{+}_5H\ .\ B$
(15) $n\text{-}C_{12}H_{25}-CH(OH)-CH(OH)-CH_3\ .\ 2B$ In the formulae 1) to 15), "i" denotes that mixtures of different branched isomers can be involved. The symbols B and Q have the meanings defined above. The symbol Z signifies 2-ethylhexyl.

The compounds of the formula I can be produced in a manner known per se; they can be produced for example by a process analogous to that described in German Offenlegungsschrift No. 2,739,312.

In the most simple case, m mols of the hydrophilić adduct component B, $H_2O_2$, $N_2H_4$ or $NH_2OH$, are mixed with approximately one mol of A, a process which is suitable particularly in the case of liquid ligands. The symbol m has in this connection the meaning defined above.

If the ligands A are solid substances, the adduct components are either reacted in an inert nonpolar solvent or reacted directly in the melt. If a solvent is used, suitable solvents are above all those of low polarity and high volatility, such as hexane, heptane, methylene chloride or toluene. If the compounds contain water, this can be removed for example azotropically, or water-binding agents, such as sodium sulfate or magnesium sulfate, can be used. The last-mentioned water-separating method is suitable in particular for hydrazine adducts and hydroxylamine adducts.

The ligands A used for the reaction methods mentioned are known compounds, and in many cases are available commercially.

Compared with similar systems, the compounds of the formula I have advantages which have been described in detail in the foregoing. It has been possible to achieve an optimum not hitherto attained, not only with regard to transportability and to storage stability, but also with regard to industrial hygiene.

The compounds of the formula I are valuable redox partners in the most general sense. They are technically very suitable for example for use as initiators for polymerisation reactions initiated by radicals, either per se, that is to say, by way of thermal or photolytic decomposition, or alternatively in combination with other redox partners as redox initiators. The hydrogen peroxide adducts can also be used as specific oxidising agents for oxidation reactions in organic media, such as epoxidation, or in the case of conversion of mercaptans to disulfides; or furthermore as washing and hygiene auxiliaries, for example as bleaching agents in detergents or as disinfectants, for example in medicinal soaps, or the adducts can be used as plant protective products, for example as total herbicides in spraying or aerosol processes, or as defoliating agents.

The Examples which follow further illustrate the present invention. In the Examples, Q has the meaning defined in the foregoing, and the index "i" signifies that mixtures of different branched isomers can be involved.

Example 1

34.5 g of a glycerol monoalkylether of the formula $n\text{-}C_{18}H_{37}-O-(CH_2-Q-O)-H$ is heated at 70° C., with stirring, until a clear melt is formed, and 5 ml of 70% aqueous hydrogen peroxide solution is added dropwise. After rapid cooling to 20° C., the $H_2O_2$ content is iodometrically determined (method according to D. H. Wheeler, Deutsche Gesellschaft für Fettforschung-Standard Method C-VI 6 a) [German Association for Fat Research].

$H_2O_2$ content: 7.8%; wax-like substance; m.p. 66° C. (Compound No. 1).

Compounds 2 and 3 are produced in an analogous manner:

| Comp. No. | Ligand | Content of $H_2O_2$ (%) | m | Physical Data |
|---|---|---|---|---|
| 2 | $n\text{-}C_{18}H_{37}-O-(CH_2-Q-O)-H$ | 8 | 0.8 | m.p. 66° C. |
| 3 | $n\text{-}C_{13\text{-}16}H_{27\text{-}33}-CH(OH)-CH_2(OH)$ | 8.8 | 0.8 | m.p. 49° C. |

EXAMPLE 2

33.6 g of glycerol mono-i-tridecyl ether is dissolved in 235 g of n-heptane (12.5% solution), and 70% aqueous hydrogen peroxide solution is added dropwise at 20° C., with stirring, until the mixture becomes cloudy. The consumption of hydrogen peroxide solution is 9.5 ml. The mixture is subsequently concentrated at 30° C. in a rotary evaporator until a constant weight is obtained. The $H_2O_2$ content in the residue (40.8 g) is determined iodometrically. $H_2O_2$ content: 14.1%; colourless liquid (Compound No. 4).

EXAMPLE 3

27.3 ml of 68% aqueous hydrogen peroxide solution is added with stirring to 100 g of a 50% solution of glycerol mono-2-ethylhexyl ether until the mixture becomes cloudy, and the solvent is subsequently distilled off at a bath temperature of 30° C. in a rotary evaporator. The mixture is subsequently rotated in an oil-pump vacuum for a further 15 minutes. To the mixture is then added 4 times 50 g of n-heptane each time, and the mixture is concentrated under the same conditions as those previously described. The residue is 72.2 g; colourless liquid; $H_2O_2$ content: 28.6% (m: 2.8) (Compound No. 5).

The compounds 6–13 are produced in an analogous manner:

| Compound No. | Ligand | Content of $H_2O_2$ (%) | m | Physical data |
|---|---|---|---|---|
| 6 | $Z-O-CH_2-CH(OH)-CH_2(OH)$ | 33 | 3.9 | colourless liquid |
| 7 | as Compound No. 6 | 29.4 | 2.9 | colourless liquid |
| 8 | as Compound No. 6 | 28.4 | 2.8 | colourless liquid |
| 9 | as Compound No. 6 | 22.6 | 2.1 | colourless liquid |
| 10 | as Compound No. 6 | 17.5 | 1.8 | colourless liquid |
| 11 | $i\text{-}C_{13}H_{27}-O-CH_2-CH(OH)-CH_2(OH)$ | 20.4 | 2.4 | colourless liquid |
| 12 | as Compound No. 11 | 19.0 | 2.2 | colourless liquid |
| 13 | as Compound No. 11 | 10.7 | 1.4 | colourless liquid |

In the compounds 6 to 10, the symbol Z denotes 2-ethylhexyl.

EXAMPLE 4

23 g of Compound No. 9 is stirred in 100 ml of heptane with 20.2 g of n-laurylmercaptan for 4 hours. The reaction proceeds slightly exothermically; the temperature rises within 2 hours from 23° C. to 32° C. The mixture is subsequently concentrated in a rotary evaporator, and the residue is recrystallized cold from 150 ml of i-propanol: di-n-lauryl disulfide; yield: 15.2 g (75.5% of theory); m.p. 32°–33° C. (Lit. 30°–31° C.).

EXAMPLE 5

86 mg of Compound No. 12 is added in a round-bottomed flask to 86 g of methyl acrylate which has been freed from the stabiliser by distillation under nitrogen. After an ascending tube has been mounted, the flask is heated under nitrogen to 100° C. Polymerisation is virtually complete after 90 minutes.

EXAMPLE 6

Testing of stability of hydrogen peroxide/1,2-diol adducts

The decomposition temperature is determined by means of a DIFFERENTIAL SCANNING CALORIMETER (Perkin-Elmer) (temperature program: 20° C./min.).

| Ligand | $H_2O_2$-content (%) | m.p. (°C.) | Decomposition temperature (°C.) |
|---|---|---|---|
| $^iC_{13}H_{27}-O-CH_2-CH(OH)-CH_2(OH)$ | 16.8 | liquid | 96 |
| $^nC_{18}H_{37}-O-(CH_2-Q-O)-H$ | 8 | 66 | 124 |
| $^nC_{13\text{-}16}H_{27\text{-}33}-CH(OH)-CH_2(OH)$ | 8.8 | 49 | 117 |

EXAMPLE 7

Testing of stability of hydrogen peroxide/1,2-diol adducts (elevated temperature: 60° C.)

The products are kept for 64 hours in a heated drying chamber, and the $H_2O_2$ content is subsequently determined iodometrically.

| Ligand | Content of $H_2O_2$ in adduct after (hours) 0 | 64 |
|---|---|---|
| Z—O—$CH_2$—CH(OH)—$CH_2$(OH) | 32.7 | 30.8 |
| $^{i}C_{13}H_{27}$—O—$CH_2$—CH(OH)—$CH_2$(OH) | 19.5 | 19.1 |
| comparison $H_2O_2$ | 30.6 | 27.6 |

Z:2-ethylhexyl.

EXAMPLE 8

Testing of stability of hydrogen peroxide/1,2-diol adducts (room temperature)

The products are kept in closed glass containers in daylight. Specimens are taken at specific intervals of time, and their $H_2O_2$ content is determined iodometrically.

| Ligand (1,2-diol) | Content of $H_2O_2$ in the adduct in % after weeks 0 | 4 | 8 | 32 |
|---|---|---|---|---|
| Z—O—$CH_2$—CH(OH)—$CH_2$(OH) | 33 | 32.5 | 31.9 | 26.5 |
| $^{i}C_{13}H_{27}$—O—$CH_2$—CH(OH)—$CH_2$(OH) | 20.4 | 20.1 | 19.1 | 17.3 |
| n-$C_{12}H_{25}$—O$\leftarrow$$CH_2$—$CH_2$—O$\rightarrow_{3.75}$H | 17.9 | 17.3 | 17.2 | 17.2 |
| comparison $H_2O_2$ | 31.5 | 29.8 | 28.5 | 23 |

Z:2-ethylhexyl.

What is claimed is:

1. A compound of formula I $$A \cdot mB \quad (I)$$

wherein

A is a compound of formula III $$R_1—X—(CH_2—Q—O)_nH \quad (III)$$

m is a rational number between 0.8 and 4.0,
B is $H_2O_2$,
$R_1$ is alkyl of 3 to 18 carbon atoms,
X is —O—,
n is 1 or 2, and
Q is —CH(OH)$CH_2$—.

2. A compound according to claim 1 of the formula I, wherein m is a rational number between 0.8 and 2.0, and the remaining symbols have the meanings defined.

3. A compound according to claim 1, (2-ethylhexyl)—O—$CH_2$—CH(OH)—$CH_2$(OH). $2H_2O_2$.

4. A compound according to claim 1, i-$C_{13}H_{27}$—O—$CH_2$—CH(OH)—$CH_2$(OH). $2H_2O_2$.

* * * * *